United States Patent [19]
Ogawa et al.

[11] Patent Number: 6,040,426
[45] Date of Patent: Mar. 21, 2000

[54] HUMAN TH2 SPECIFIC PROTEIN

[75] Inventors: Kazuyuki Ogawa; Kazuya Tanaka; Kinya Nagata; Syoichi Takano, all of Saitama, Japan

[73] Assignee: BML, Inc., Tokyo, Japan

[21] Appl. No.: 08/981,825

[22] PCT Filed: Jun. 5, 1997

[86] PCT No.: PCT/JP97/01906

§ 371 Date: May 11, 1998

§ 102(e) Date: May 11, 1998

[87] PCT Pub. No.: WO97/46677

PCT Pub. Date: Dec. 11, 1997

[30] Foreign Application Priority Data

Jun. 5, 1996 [JP] Japan ...................................... 8-166793

[51] Int. Cl.[7] .................................................. C07K 14/435
[52] U.S. Cl. ............................................................ 530/350
[58] Field of Search ............................................... 530/350

[56] References Cited
PUBLICATIONS

Ngo et al.; The Protein Folding Problem and Tertiary Structure Prediction; p. 491–495, 1994.
Xu et al.; J. Exp. Med.; vol. 187; No. 5; p. 787–794, 1998.
Yoshida et al.; Hybridoma; vol. 14; No. 5; p. 419–427, 1995.

*Primary Examiner*—Christina Y. Chan
*Assistant Examiner*—Amy DeCloux
*Attorney, Agent, or Firm*—Knobbe, Martens Olson & Bear, LLP

[57] ABSTRACT

The present invention provides for specifying the condition and type of immune-related diseases on the basis of the knowledge about the polarization of the distribution of helper T-cell subsets Th1 and Th2. More sepcifically, in this invention, the gene (B19) specific only the human Th2 is prepared and specified by a subtraction method, and a recombinant vector into which the gene is incorporated, a transformant transformed by the recombinant vector, a human-Th2-specific protein which the gene encodes and which derives from the transformant, and a monoclonal antibody against the Th2-specific protein are produced and the gene, protein, antibody, etc. are used as the means for specifying or correcting the polarization of the distribution of Th1 and Th2 to solve the above object.

1 Claim, 4 Drawing Sheets

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 21 base pairs
      (B) TYPE: nucleic acid
      (C) STRANDEDNESS: single
      (D) TOPOLOGY: linear    (xi) SEQUENCE DESCRIPTION: SEQ ID NO:1:

AGTTACACGT CTAGAATGGC T                                                           21

(2) INFORMATION FOR SEQ ID NO:2:

(i) SEQUENCE CHARACTERISTICS:
      (A) LENGTH: 25 base pairs
      (B) TYPE: nucleic acid
      (C) STRANDEDNESS: single
      (D) TOPOLOGY: linear    (xi) SEQUENCE DESCRIPTION: SEQ ID NO:2:

AGCCATTCTA GACGTGTAAC TGATA                                               25

(2) INFORMATION FOR SEQ ID NO:3:

(i) SEQUENCE CHARACTERISTICS:
      (A) LENGTH: 21 base pairs
      (B) TYPE: nucleic acid
      (C) STRANDEDNESS: single
      (D) TOPOLOGY: linear    (xi) SEQUENCE DESCRIPTION: SEQ ID NO:3:

CTCTTGCTTG AATTCGGACT A                                                           21

(2) INFORMATION FOR SEQ ID NO:4:

(i) SEQUENCE CHARACTERISTICS:
      (A) LENGTH: 25 base pairs
      (B) TYPE: nucleic acid
      (C) STRANDEDNESS: single
      (D) TOPOLOGY: linear    (xi) SEQUENCE DESCRIPTION: SEQ ID NO:4:

TAGTCCGAAT TCAAGCAAGA GCACA                                               25

(2) INFORMATION FOR SEQ ID NO:5:

(i) SEQUENCE CHARACTERISTICS:
      (A) LENGTH: 2911 base pairs
      (B) TYPE: nucleic acid
      (C) STRANDEDNESS: both
      (D) TOPOLOGY: unknown    (ii) MOLECULE TYPE: cDNA (xi) SEQUENCE DESCRIPTION: SEQ ID NO:5:

```
CAGCCTCCCT CTCCCACCTC TGTCTGCCCG CTGCCTCTTG TCTAGCTGCT GTCAGGAGCT      60
GACTGCCTCC AGGGCTGGAA TCCTGTGCTC CCTCTGTGCC CAGAGCCCCA CGATGTCGGC     120
CAACGCCACA CTGAAGCCAC TCTGCCCCAT CCTGGAGCAG ATGAGCCGTC TCCAGAGCCA     180
CAGCAACACC AGCATCCGCT ACATCGACCA CGCGGCCGTG CTGCTGCACG GGCTGGCCTC     240
GCTGCTGGGC CTGGTGGAGA ATGGAGTCAT CCTCTTCGTG GTGGGCTGCC GCATGCGCCA     300
GACCGTGGTC ACCACCTGGG TGCTGCACCT GGCGCTGTCC GACCTGTTGG CCTCTGCTTC     360
CCTGCCCTTC TTCACCTACT TCTTGGCCGT GGGCCACTCG TGGGAGCTGG GCACCACCTT     420
CTGCAAACTG CACTCCTCCA TCTTCTTTCT CAACATGTTC GCCAGCGGCT TCCTGCTCAG     480
CGCCATCAGC CTGGACCGCT GCCTGCAGGT GGTGCGGCCG GTGTGGGCGC AGAACCACCG     540
CACCGTGGCC GCGGCGCACA AGTCTGCCT GGTGCTTTGG GCACTAGCGG TGCTCAACAC     600
GGTGCCCTAT TTCGTGTTCC GGGACACCAT CTCGCGGCTG ACGGGCGCA TTATGTGCTA     660
CTACAATGTG CTGCTCCTGA ACCCGGGGCC TGACCGCGAT GCCACGTGCA ACTCGCGCCA     720
GGCGGCCCTG GCCGTCAGCA AGTTCCTGCT GGCCTTCCTG GTGCCGCTGG CGATCATCGC     780
CTCGAGCCAC GCGGCCGTGA GCCTGCGGTT GCAGCACCGC GGCCGCCGGC GGCCAGGCCG     840
CTTCGTGCGC CTGGTGGCAG CCGTCGTGGC CGCCTTCGCG CTCTGCTGGG GCCCTACCA     900
CGTGTTCAGC CTGCTGGAGG CGCGGGCGCA CGCAAACCCG GGGCTGCGGC CGCTCGTGTG     960
GCGCGGGCTG CCCTTCGTCA CCAGCCTGGC CTTCTTCAAC AGCGTGGCCA ACCCGGTGCT    1020
CTACGTGCTC ACCTGCCCCG ACATGCTGCG CAAGCTGCGG CGCTCGCTGC GCACGGTGCT    1080
GGAGAGCGTG CTGGTGGACG ACAGCGAGCT GGGTGGCGCG GGAAGCAGCC GCCGCCGCCG    1140
CACCTCCTCC ACCGCCCGCT CGGCCTCCCC TTTAGCTCTC TGCAGCCGCC CGGAGGAACC    1200
GCGGGGCCCC GCGCGTCTCC TCGGCTGGCT GCTGGGCAGC TGCGCAGCGT CCCCGCAGAC    1260
GGGCCCCCTG AACCGGCGC TGAGCAGCAC CTCGAGTTAG AACCGGCCC ACGTAGGGCG    1320
GCACTCACAC GCGAAAGTAT CACCAGGGTG CCGCGGTTCA ATTCGATATC CGGACTCCTG    1380
CCGCAGTGAT CAAAGTCCGA GGGGCGGGAC CCAGGCACCT GCATTTTAAA GCGCCCCGGG    1440
AGACTCTGAA TCTTTTTCAG AAACAGTGAG TTAAAGCAGT GCTTCTCAAA CCTTGATGTG    1500
CCTGTGAATC ACCTAGGGGT CTTGTTAAGT GCAGTCTGAT CCAGGAGGCC GGGGCCGGGT    1560
ACTGAGAGTC TGCACTTAAC AAGCTCCCAG GCCGAGAAGC CAGTGCGGCA GGTTCACAGG    1620
CGAGGCCTGG AGTAACACAA AGTGAAACTC GTAATAGACT TCCCACTCTA GGGCAGTGGA    1680
GTCGGAAGGG CACACGGGGT GCGTCTCCCC GGAGTTCAGT TTTACCAGAT GATGGGGGAG    1740
GGGGGAAGGA GTTTTATGTT AAACCATCCA TGTATTTTTG GAGAAGAGAG AGGAAAGGTT    1800
TGAGAAGCAC TGTTCCAGCC TGCCCTCTTC ATTTAGCCAA TGCTTACTGC GCTAGACGCT    1860
TCATCCCACA ATCTTAAGGG GCAGCTTCTA TTAGCCAGTC TTTACAGCTG AGCACATTCT    1920
GGCTCAGGGA GGTTAAGTGA CTTGCCCAGT TTCAGGGCTA ACGACCACAG GGTCTGCACT    1980
CTAACCCTAG GCATCACATG CTCAATGACT CTCTGGTGAG CGAGGACATT CTCTGACCTA    2040
CTCGAGGGAC TTAAGATGCT ACCTTGTGAC CCAGCACTGC CCAAAGTGCT TCCAAGGCAG    2100
AAGCAGCAGG GGATGGCGTG GTCAAGCACT CGGGAAACCT GGGGCTAATC AAATCCAATG    2160
GGGGAAATGA CTAAAAGTCT TCGGTCGTTA GAAGTTGAAT GGGCACAGCA ACTCTAAGAC    2220
TACAGCACAC GTCATTTCTT AGCTAAGCGG ACCAGCCTCC CTGTCGGCCT GGTGTTCTGT    2280
```

-continued

```
GGGATCCCTC TGGGCACTGG TAATCCCAAG ATCTGTGCAG CCCCGCCTCC AGGCCACATG    2340

GGGCTGGGCA GCTACCATTT CCCTTTTGCG GATGGGAGGG GTAACTTGCA CCTCTGACCT    2400

ATCACTTCCA CTGCACCCCG TCTCATTCCT CCACCTGCCG TGGACTTGGG GTCAGAGACT    2460

GCTGTGTTTG AGCTCTGCAG CCCAGGGACC GAAAAGTTGG TGTCAATGAA TTTTGCTTGG    2520

TGGATGAAAT GTCAGTGGAA GAAGCAGATG AGAAACTCTT GAGATCTTGG TCCTGTGTTT    2580

TTTCTGCCAC CAAAGGCCAG GGTCACTGAA GGCCTGGCCC ACAGCAGGTG CTGAGCAAAG    2640

GGAACAGTGA GGTGCCCAGC TAGCTGCAGA GCCACCCTGT GTTGACACCT CGCCCCTGCT    2700

CCCTCCCATC CCTTCCCCCT TTACTCATAG CACTTCCCCC ATTGGACACG TGGTGCATTT    2760

TGCTTGTTTA TTATGTTTTC TCTCCATCAG AATGAAAGCT CCTCGAGGGC AGGGACTTTG    2820

GTCTATTGTC TGTATTTGCC GGTGCCTAGG ATTGTGCCTG TATGCAACAG GCACTCAATA    2880

AATATTTTTG CTGTAGACTG GAAAAAAAAA A                                   2911
```

(2) INFORMATION FOR SEQ ID NO:6:

(i) SEQUENCE CHARACTERISTICS:
        (A) LENGTH: 395 amino acids
        (B) TYPE: amino acid
        (C) STRANDEDNESS: unknown
        (D) TOPOLOGY: unknown     (ii) MOLECULE TYPE: protein     (xi) SEQUENCE DESCRIPTION: SEQ ID NO:6:

```
Met Ser Ala Asn Ala Thr Leu Lys Pro Leu Cys Pro Ile Leu Glu Gln
  1               5                  10                  15

Met Ser Arg Leu Gln Ser His Ser Asn Thr Ser Ile Arg Tyr Ile Asp
             20                  25                  30

His Ala Ala Val Leu Leu His Gly Leu Ala Ser Leu Leu Gly Leu Val
         35                  40                  45

Glu Asn Gly Val Ile Leu Phe Val Val Gly Cys Arg Met Arg Gln Thr
     50                  55                  60

Val Val Thr Thr Trp Val Leu His Leu Ala Leu Ser Asp Leu Leu Ala
 65                  70                  75                  80

Ser Ala Ser Leu Pro Phe Phe Thr Tyr Phe Leu Ala Val Gly His Ser
                 85                  90                  95

Trp Glu Leu Gly Thr Thr Phe Cys Lys Leu His Ser Ser Ile Phe Phe
            100                 105                 110

Leu Asn Met Phe Ala Ser Gly Phe Leu Leu Ser Ala Ile Ser Leu Asp
        115                 120                 125

Arg Cys Leu Gln Val Val Arg Pro Val Trp Ala Gln Asn His Arg Thr
    130                 135                 140

Val Ala Ala Ala His Lys Val Cys Leu Val Leu Trp Ala Leu Ala Val
145                 150                 155                 160

Leu Asn Thr Val Pro Tyr Phe Val Phe Arg Asp Thr Ile Ser Arg Leu
                165                 170                 175

Asp Gly Arg Ile Met Cys Tyr Tyr Asn Val Leu Leu Leu Asn Pro Gly
            180                 185                 190

Pro Asp Arg Asp Ala Thr Cys Asn Ser Arg Gln Ala Ala Leu Ala Val
        195                 200                 205

Ser Lys Phe Leu Leu Ala Phe Leu Val Pro Leu Ala Ile Ile Ala Ser
    210                 215                 220

Ser His Ala Ala Val Ser Leu Arg Leu Gln His Arg Gly Arg Arg Arg
225                 230                 235                 240
```

```
Pro Gly Arg Phe Val Arg Leu Val Ala Ala Val Val Ala Ala Phe Ala
            245                 250                 255

Leu Cys Trp Gly Pro Tyr His Val Phe Ser Leu Leu Glu Ala Arg Ala
            260                 265                 270

His Ala Asn Pro Gly Leu Arg Pro Leu Val Trp Arg Gly Leu Pro Phe
            275                 280                 285

Val Thr Ser Leu Ala Phe Phe Asn Ser Val Ala Asn Pro Val Leu Tyr
            290                 295                 300

Val Leu Thr Cys Pro Asp Met Leu Arg Lys Leu Arg Arg Ser Leu Arg
305                 310                 315                 320

Thr Val Leu Glu Ser Val Leu Val Asp Asp Ser Glu Leu Gly Gly Ala
            325                 330                 335

Gly Ser Ser Arg Arg Arg Thr Ser Ser Thr Ala Arg Ser Ala Ser
            340                 345                 350

Pro Leu Ala Leu Cys Ser Arg Pro Glu Glu Pro Arg Gly Pro Ala Arg
            355                 360                 365

Leu Leu Gly Trp Leu Leu Gly Ser Cys Ala Ala Ser Pro Gln Thr Gly
            370                 375                 380

Pro Leu Asn Arg Ala Leu Ser Ser Thr Ser Ser
385                 390                 395
```

HUMAN TH2 SPECIFIC PROTEIN

TECHNICAL FIELD

The present invention relates to a Th2-specific-protein and a gene encoding the protein, and transformants, recombinant vectors and monoclonal antibodies related to the gene.

More specifically, the present invention relates to a protein which is specific solely for Type 2 helper T cells and which can be used as means for promptly and simply specifying variations in balance among helper T cell subsets intimately involved in the occurence of atopic diseases, the progression of AIDS, etc., and also relates to a gene which encodes this protein.

Further, the present invention relates to a recombinant vector which harbors the gene and is used for expressing it, as well as to a transformant which is transformed with the recombinant vector.

Furthermore, the present invention relates to a monoclonal antibody against the Th2-specific protein, and a hybridoma which produces the monoclonal antibody.

BACKGROUND ART

Immunology has made a remarkable progress in recent years and has added a great contribution to the field of medicine.

Studies of immunology have revealed that cytokines produced by macrophages, lymphocytes, etc. play the central role in promoting or suppressing every immunological reaction, such as infection immunity, tumor immunity, allergies, or anaphylaxis.

Mosmann and Coffman, et al. classified CD4$^+$ T-cell clones which are established from mouse spleen cells and can be cultured for a long period of time into two different types of subsets according to the difference between cytokines produced by the clones (Mosmann, T. R., et al., J. Immunol.,136, 2348 (1986)).

Specifically, they classified CD4$^+$ T-cell clones into the "T-helper 2 (Th2) subset" and the "T-helper 1 (Th1) subset": the former principally produces IL(interleukin)-4, IL-5, IL-6, IL-10 and IL-13; and the latter principally produces IL-2, IFN (interferon)-$\gamma$, and TNF (tumor necrosis factor)-$\beta$.

Although the existence of such subsets of helper T cells in humans was initially deemed dubious, it is now well accepted (Romagnani, S., Immunology Today 12, 256 (1991), etc.).

Nowadays, the nature and functions of the helper T-cell subsets Th2 and Th1 in mice or humans are becoming much more evident. In terms of biological significance, they have become of great interest as dominant cells which control different immunological reactions.

In many infectious diseases or immunological diseases, polarization is observed in the distribution of the Th1/Th2 subsets of lymphocytes of patients; i.e., an extreme bias arises in the distribution toward either one of the subset Th1 or Th2. Therefore, it is suggested that the nature of this polarization phenomenon may reflect the condition and type of the disease.

For example, the following are currently becoming distinct:
(1) In the case of Mycobacterium diseases, if immunological reactions with respect to Mycobacterium are mainly delayed-type hypersensitivity (DTH) reactions, the Th1 subset is dominant, whereas if the immunological reactions are chronic and progressive, the Th2 subset is dominant. (2) In the case of HIV diseases, the production of Th1-type cytokines is observed among many long-term nonprogressive HIV-infected patients. If polarization arises toward the Th2 subset, the symptoms of the diseases become progressive or fulminated. (3) With regard to patients having atopic diseases, if there arises polarization toward the Th2 subset, the diseases become aggravated.

In view of the foregoing, the problems to be solved by the present invention is to provide means for specifying the condition and type of immune-related diseases on the basis of the knowledge about the polarization of the distribution of Th1/Th2 subsets (hereinafter referred to as Th1/Th2 imbalance).

DISCLOSURE OF INVENTION

The inventors of the present invention carried out extensive studies on the above-described problems. As a result, they found that if a protein specific for Th2 cells, a gene which encodes the Th2-specific protein, a protein specific for Th1 cells, and a gene which encodes the Th1-specific protein can be identified and prepared, respectively, it becomes possible to provide means for specifying the condition and type of an immunity-related disease of interest through use of the proteins and genes. The present invention was completed on the basis of this finding.

The present invention is directed to a protein specific for human Th2 cells and a gene (B19) which encodes the human-Th2-specific protein.

More specifically, the present inventors provide the invention as follows:

According to a first aspect of the present invention, there is provided a human-Th2-specific protein having an amino acid sequence represented by sequence ID No. 6.

According to a second aspect of the present invention, there is provided a human-Th2-specific protein which has an amino acid sequence corresponding to an amino acid sequence represented by sequence ID No. 6 partially deleted, replaced, or added, and which has substantially the same biological activities as those of the human-Th2-specific protein.

According to a third aspect of the present invention, there is provided a human-Th2-specific gene which contains a nucleotide sequence coding for the amino acid sequence represented by sequence ID No. 6.

According to a fourth aspect of the present invention, there is provided a human-Th2-specific gene containing a nucleotide sequence represented by sequence ID No. 5.

According to a fifth aspect of the present invention, there is provided a human-Th2-specific gene which contains a nucleotide sequence corresponding to a nucleotide sequence represented by sequence ID No. 5 partially deleted, replaced, or added; which hybridizes with DNA having the nucleotide sequence represented by sequence ID No. 5 under stringent conditions; and which encodes a human-Th2-specific protein having substantially the same biological activities as those of a human-Th2-specific protein having the amino acid sequence represented by sequence ID No. 6.

According to a sixth aspect of the present invention, there is provided a recombinant vector for expressing a gene, which vector contains the human-Th2-specific gene as defined in any one of the aforementioned aspects.

According to a seventh aspect of the present invention, there is provided a transformant which is transformed by the recombinant vector defined in the sixth aspect and in which the human-Th2-specific gene contained in the recombinant vector is expressed.

According to an eighth aspect of the present invention, there is provided a monoclonal antibody which takes as its antigenic determinant any portion of the human-Th2-specific protein defined in the above aspects and which does not exhibit immunoreactivity with respect to human-Th1-specific proteins.

According to a ninth aspect of the present invention, there is provided a hybridoma which produces the monoclonal antibody defined in the eighth aspect.

The following will explain the mode for carring out the present invention.

As described hereinabove, a human Th2 from which human-Th2-specific gene used herein is derived is one of the subsets of human helper T cells. The human-Th2-specific gene will be hereinafter referred to as a Th2 (B19) gene. Unless otherwise specified, the Th2 (B19) gene includes an altered human-Th2 (B19)-specific gene (which will be described later) that falls within the scope of the present invention.

The human Th2 is a subset of helper T cells having the following properties:

(1) The human Th2 cells produce IL-4 and IL-5 but produces neither IFN-γ nor TNF-β.

(2) The human Th2 cells proliferate in response to IL-2 and IL-4, and the induction of the human Th2 cells are suppressed by IFN-γ. Although the other subset (i.e., the human Th1 subset) proliferates similarly in response to IL-2 (as well as with IL-12), the induction of the human Th1 cells are suppressed by IL-4 as contrasted with the human Th2 cells.

(3) Surface markers for human Th2 cells which can definitely distinguish Th2 cells from Th1 cells are not yet found. The human Th2 cells, like the human Th2 cells, have phenotypes of $CD44^{bright}$, $CD45RB^{dull}$, and $LECAM-1^{dull}$.

(4) The human Th2 cells encourage antibody production and induces, particularly, IgE production.

(5) The human Th2 cells promote the differentiation and proliferation of mast cells and eosinophils.

(6) The human Th2 cells do not induce antigen-specific DTH reaction and become dominant if immunological reactions are chronic and progressive.

The Th2 (B19) gene of the present invention can be obtained by establishing human Th2 clones having the above-described characteristics and producing a cDNA library of the human Th2 cells from the thus-established human Th2 clones.

A. Establishment of the Human Th2 Clones:

As a preceding step for establishing desired human Th2 clones, a $CD4^+$ T-cell population which is known to contain these clones is produced.

The $CD4^+$ T cell population can be produced according to a conventional method disclosed, for example, in "Gianfranco, F. D. P., et al., J. Clin. Invest. 88, 346 (1991)."

More specifically, for example, peripheral blood mononuclear cells may be separated from the whole blood of humans, and the thus-separated peripheral blood mononuclear cells may be stimulated by various T-cell-activators to thereby produce a desired $CD4^+$ T-cell population. The T-cell-activators may include; e.g., non-specific T-cell-activators such as kidney bean-derived phytohemagglutinin (PHA); cytokines such as IL-2, IL-4, or IL-12; or stimulus antigens such as PPD or mite extracts.

Prior to isolation of $CD4^+$ T cell clones, which will be described below, the $CD4^+$ T cell population is preferably subjected to removal of elements other than the $CD4^+$ T cells; e.g., $CD8^+$ T cells. For example, there can be employed a method for concentrating only the $CD4^+$ T cells through use of magnetic beads coupled to anti-CD4 antibody.

After completion of the above-described induction process, the $CD4^+$ T-cell clones are isolated. They can be isolated according to methods known per se such as the limiting dilution technique.

More specifically, for example, cells are seeded in a medium including a PHA and IL-2 on a 96-well microplate so as to be 0.5 to 10 cells/well. The medium is replaced with a fresh IL-2-added medium every three to four days. The surface marker of the cells which have been ascertained to proliferate (normally within two to four weeks) is examined. $CD4^+$ T-cell clones can be isolated by selecting only the CD4-positive clones.

From among the thus-isolated $CD4^+$ T-cell clones, human Th2 clones of interest can be selected.

The human Th2 clones are selected from the $CD4^+$ T-cell clones according the known differences in properties between the human Th2 and human Th1 cells.

Specifically, for example, clones which produce IL-4 in response to the stimulation of anti-CD3 antibody but do not produce IFN-γ can be selected as the human Th2 clones. (In contrast, clones which produce IFN-γ but do not produce IL-4 are selected as the human Th1 clones.)

B. Preparation of Human-Th2-specific cDNA:

With regard to the cDNA of the human Th2 and that of the human Th1, it is anticipated that there exist nucleotide sequences common to both types of cDNA and nucleotide sequences specific for the respective types.

To prepare cDNA specific for the human Th2 cells of interest on the basis of such an anticipation, it is advantageous to use a so-called subtraction method by which cDNA species common to the human Th1 and human Th2 cells are eliminated from cDNA molecules of the human Th2 cells.

The subtraction method may include, e.g., a method reported by Davis et al., (Davis, M. M. et al., Proc. Natl. Acad. Sci. U.S.A., 81, 2194 (1984)).

This method is intended to concentrate cDNA clones specific for one of two cell types, through hybridization of the cDNA to be subtracted with a greatly excessive amount of poly $(A)^+$ RNA derived from the other cell type, and the screening of the cDNA library through use of non-hybridized residual cDNA as a probe.

Since this method requires a large amount of poly $(A)^+$ RNA, the method has a disadvantage of being difficult to carry out the method if a large quantity of poly $(A)^+$ RNA is not readily available.

To overcome this problem, another method has already been reported which uses the PCR technique in order to carry out subtraction through use of a comparatively small amount of poly (A)⁺ RNA as a starting material [e.g., a gene expression screen method (Wang, Z. and Brown, D. D., Proc. Natl. Acad. Sci. U.S.A.,88, 11505 (1991), etc.]. This method is characterized by the amplification of cDNA serving as a starting material by use of the PCR method. This method also has the advantage of being capable of cloning a very small amount of mRNA through repetition of the subtraction operation and the amplifying operation by PCR.

In general, culturing a large amount of normal CD4⁺ T-cell clones and securing a large amount of mRNA which serves as a template of cDNA is difficult. For this reason, the present invention preferably employs the "gene expression screen method," for example, from among the aforementioned subtraction methods.

More specifically, cDNAs derived from human Th2 clones and human Th1 clones are prepared by generally known methods (e.g., a method in which a reverse transcriptase is used, with poly (A)⁺ RNA being employed as a template of cDNA), and the resultant cDNAs are amplified by PCR.

In amplifying cDNA, it is desirable to previously subject the cDNA to treatment with restriction enzymes or ultrasonic treatment so as to obtain cDNA fragments which are suitable in length for amplification according to the PCR method.

For example, specific primers which contain different nucleotide sequences respectively for the human Th1 and the human Th2 cells may be used as the PCR primers needed to amplify cDNA according to the PCR method. Usually, these specific primers are prepared by chemical synthesis. Since only the human-Th2-derived cDNA is amplified through use of a specific primer after the subtraction, this method has the advantage of minimizing the amplification of a trace amount of human-Th1-derived cDNA which may contaminate the human-Th2-derived cDNA.

In this case, it is necessary to previously connect linker—which contain sequences capable of being annealed with the PCR prime—to both ends of the cDNA fragments. Therefore, in the aforementioned fragmentation, it is desirable to use a restriction enzyme which produces cDNA fragments having terminals capable of being linked with the linkers.

After the cDNA fragments derived from the human Th1 and Th2 clones have been attached to the PCR linkers, fragments having a certain length are selected from among the cDNA fragments by suitable fractionation methods such as agarose gel electrophoresis. The thus-chosen cDNA fragments are amplified by the PCR method, whereby the amplified cDNA fragments can be used as a starting material for subtraction.

With the thus-prepared cDNA fragments, a gene library containing the human Th2 gene of interest according to the present invention can be prepared by subtracting the cDNA fragments which have the nucleotide sequences common to the human Th1 and Th2 from the human-Th2-clone-derived cDNA fragments.

This selection may be performed by hybridizing a given quantity of human-Th2-clone-derived cDNA fragments with an excessive quantity of labeled cDNA fragments which are derived from the human Th1 clones. The cDNA hybridized with the human-Th1-clone-derived cDNA fragments can be eliminated according to the labels, and the remaining cDNA fragments can be handled as cDNA fragments based on the nucleotide sequence specific solely for the human Th2 cells.

The labels used herein are not limited to any particular labels, so long as they allow the use of the foregoing screening method. Needless to say, it is preferable to use means which enables easy labeling and easy removal of the label. In this respect, it is preferable to use a method in which cDNA fragments are labeled, for example, with biotin, and the resultant labeled cDNA fragments are caused to be adsorbed onto streptavidin.

The thus-screened cDNA fragments based on the nucleotide sequence specific only for the human Th2 are amplified again by the PCR method and then screened by the foregoing screening means. Through repetition of these processes, the cDNA fragments of interest can be concentrated and amplified.

A gene library containing the Th2 (B19) gene of the present invention can be obtained through use of the thus-prepared cDNA fragments.

The gene library can be prepared through use of a method known per se.

Briefly, the cDNA fragments are inserted into a suitable vector used for transferring a gene, and the vector is introduced into a host corresponding to the vector, thereby enabling preparation of a gene library of interest. Here, it is possible to check whether or not the cDNA fragments have been inserted into the vector, for example, by means of the color selection based on the activity of a lac Z gene, for example, in the vector.

The vector for introduction purposes is not particularly limited. For example, useful plasmids include pBluescript, pUC18, pBR322, pBGP120, pPCφ1, pPCφ2, pPCφ3, pMC1403, pLG200, pLG300, pLG400, etc; useful λ phages include λ gt10, or λ ZAPII, etc. In consideration of ease of handling, a plasmid which contains the lac Z gene as a selection marker is preferably used. More specifically, of the above-described vectors, pBluescript, pUC18, or pBGP120 is preferably used.

The gene library may alternatively be prepared through use of a commercially available gene library preparation kit.

C. Isolation of the Th2 (B19) Gene of the Present Invention:

It is possible to directly extract DNA from the gene library prepared in the above-described manner and then to determine the sequences of some of the DNA to screen the clones containing the present Th2 (B19) gene from the sequences, but it is desirable to further screen the clones containing the present Th2 (B19) gene in advance to certainly specify the same.

As a screening method, a generally known screening method may be used. For example, there are first prepared genes derived from a gene library which has been prepared in the previous-described manner and is based on a human-Th2-specific genes, and genes derived from a gene library which has been prepared separately and is based on a human-Th1-specific genes. These genes are labeled to form labeled probes, and the labeled genes are then hybridized with a replica of the gene library based on a human-Th2-specific genes. Subsequently, clones which hybridize with a probe of the human-Th2-specific genes but does not hybridize with a probe of the human-Th1-specific genes are selected. The selected clones can be used for determining the nucleotide sequence of the Th2 (B19) gene of the present invention, which will be described later, as the clones which harbor the Th2 (B19) gene of the present invention.

To ensure extra care, there may be determined clones to be used for determination of the nucleotide sequence of the Th2 (B19) gene, which will be described later, for example, by comparison of expression patterns of mRNA through use of the Northern blotting technique in which the total RNA or poly (A)⁺ RNA of the human Th2 cells and the human Th1 cells are used.

The nucleotide sequence of the Th2 (B19) gene of the present invention contained in the thus-prepared clones can be in general determined through use of a known method.

The nucleotide sequence of the Th2 (B19) gene of interest can be determined through use of, for example, a Maxam-Gilbert method (Maxam, A. M., and Gilbert, W., Proc. Natl. Acad. Sci. U.S.A., 74, 560 (1977)), a genomic sequence method (Church, G. M. and Gilbert, W., Proc. Natl. Acad. Sci. U.S.A., 81, 1991 (1984)), a multiplex method (Church, G. M., and Kieffer-Higgins, S., Science, 240, 185 (1988)), a cycle sequence method (Murray, V., Nucleic Acids Res.,17, 8889 (1989)), or a dideoxy method (Sanger, F., et al., Proc. Natl. Acad. Sci. U.S.A., 74, 5463 (1977)).

Alternatively, as a matter of course, the nucleotide sequence may be determined through use of a nucleotide sequence automatic analyzer to which the principles of the foregoing methods are applied.

On the basis of the thus-determined nucleotide sequence of the Th2 (B19) gene, the Th2 (B19) gene itself can be obtained.

More specifically, provided that the cDNA of the human Th2 cells which serves as the source of the Th2 (B19) gene prepared in the above-described manner is used as a template, and that the DNA fragment containing the sequences on the 5'-terminal site and the 3'-terminal site of the Th2 (B19) gene determined in the previously-described manner is used as a primer, the Th2 (B19) gene can be amplified in large quantity by the aforementioned PCR method and obtained.

Alternatively, a traditional method is also available in which the full length of the Th2 (B19) gene of the present invention is obtained by selecting a clone containing the Th2 (B19) gene from the DNA gene library prepared from the human Th2 cells, with a human Th2 gene fragment itself whose nucleotide sequence has been determined being employed as a probe.

Further, the Th2 (B19) gene of the present invention can be produced by chemical synthesis through use of a generally known method such as a phosphite-triester method (Ikehara, M., et al., Proc. Natl. Acad. Sci. U.S.A.,81, 5956 (1984)). In addition, the Th2 (B19) gene can be synthesized through use of a DNA synthesizer to which the chemical synthesis method is applied.

The inventors of the present invention have realized the existence of altered genes containing the nucleotide sequence of the Th2 (B19) gene whose nucleotides are partly deleted, replaced, or added by alteration (these altered genes have a homology of about 70% or more with respect to the intact Th2 (B19) gene). Such altered genes also fall within the scope of the present invention.

A human Th2 gene which can fall within the scope of the present invention is a human-Th2-specific gene which hybridizes with DNA containing a nucleotide sequence represented by sequence ID No. 5 (which will be described later) under stringent conditions or conditions under which a hybrid between DNA is less apt to be formed in a system. More specifically, the conditions include the temperature of the system (the higher the temperature, the lower the likelihood of the hybrid being formed), the concentration of salt (the lower the salt concentration, the lower the likelihood of the hybrid being formed), and the concentration of a denaturing agent such as formamide (the higher the concentration of the denaturing agent, the lower the likelihood of the hybrid being formed). Further, the human-Th2-specific gene encodes a human-Th2 (B19)-specific protein which has substantially the identical biological activities as those of a human-Th2-specific protein containing an amino acid sequence represented by sequence ID No. 6 (which will be described later).

The term "substantially identical" used herein signifies that with regard to biological activities the human-Th2 (B19)-specific protein is qualitatively and/or quantitatively identical to human-Th2 (B19)-specific protein for comparison.

Specific biological activities of the human-Th2 (B19)-specific protein will be described later.

A gene can be altered in a desired way through use of a generally known method; e.g., a so-called site-specific mutagenesis (Mark, D. F., et al., Proc. Natl. Acad. Sci. U.S.A., 81, 5662 (1984)).

A local Th1/Th2 balance of a disease can be checked through use of the Th2 (B19) gene of the present invention produced in the above-described manner.

Specifically, a local Th1/Th2 balance of a disease can be checked by extracting mRNA from local tissue of the disease, and measuring the level of expression of the Th2 (B19) gene in the tissue through use of; e.g., an RT-PCR method ("PCR Protocols, A Guide to Methods and Applications" Innis, M. A., et al., ed., Academic Press, San Diego, 1990).

As mentioned herein under the heading "Background Art", the checking of the Th1/Th2 balance allows more reliable ascertainment of variations in the symptoms of diseases to which a Th1/Th2 imbalance is of importance; e.g., HIV diseases, allergic diseases, or various infectious diseases.

Although, as a matter of course, the Th1/Th2 balance can be checked through use of polyclonal/monoclonal antibodies specific to human Th2 cells, which will be described later, the foregoing checking means is effective in the case where the use of these antibodies is difficult; e.g., the case where the quantity of expression of the target protein is a trace amount.

D. Manufacture of the Human-Th2 (B19)-specific Protein of the Present Invention:

Through use of the thus-produced Th2 (B19) gene of the present invention, a recombinant human-Th2-specific protein (hereinafter referred to as a "human Th2 (B19) protein") can be manufactured. Unless otherwise specified, the human Th2 (B19) protein includes human-Th2-specific proteins which can be translated from the above-described altered genes. As a matter of course, these altered proteins which can be translated from the altered genes have substantially the identical biological activities as those of the unaltered human Th2 (B19) protein of the present invention.

The human Th2 (B19) protein of the present invention can be manufactured according to a generally known conventional gene recombination technique by use of the Th2 (B19) gene of the present invention.

More specifically, the Th2 (B19) gene of the present invention is inserted into a gene expression vector which is in such a form as to be able to express the Th2 (B19) gene of the present invention. The recombinant vector is transferred into a host whose properties correspond to those of the vector, whereby it is transformed. The human Th2 (B19) protein of interest can be manufactured by culturing the transformant.

Preferably, there is used herein a gene expression vector which usually possesses a promoter and an enhancer in the upstream region, and a transcription terminating sequence in the downstream region of a gene which is to be expressed.

Expression of the Th2 (B19) gene of the present invention is not limited to a direct expression system but may be accomplished in; e.g., a fused protein expression system which utilizes a β-galactosidase gene, a glutathione-S-transferase-gene, or a thioredoxin gene.

Examples of gene expression vectors include vectors whose hosts are *E. coli*, e.g., pQE, pGEX, pT7-7, pMAL, pTrxFus, pET, or pNT26CII; vectors whose hosts are *Bacillus subtilis*, e.g. pPL608, pNC3, pSM23, or pKH80; vectors whose hosts are yeast, e.g., pGT5, pDB248X, pART1, pREP1, YEp13, YRp7, or YCp 50; and vectors whose hosts are mammal cells or insect cells, e.g., p91023, pCDM8, pcDL-SRα 296, pBCMGSNeo, pSV2dhfr, pSVdhfr, pAc373, pAcYM1, pRc/CMV, pREP4, or pcDNAI.

These gene expression vectors may be selected in accordance with the purpose of expression of the human Th2 (B19) protein of the present invention. For instance, in a case where the human Th2 (B19) protein is intended to be expressed in large quantity, it is desirable to select a gene expression vector capable of choosing *E. coli, Bacillus subtilis*, or yeast as its host. In contrast, in a case where the human Th2 (B19) protein of the present invention is intended to be expressed even in a small amount so as to become active reliably, a gene expression vector capable of choosing mammal or insect cells as its host is preferably selected.

Although the existing gene expression vector can be selected as mentioned above, as a matter of course, a gene expression vector may alternatively be prepared according to the purpose of expression as required.

These recombinant vectors also fall within the scope of the present invention.

The transfer of the vector harboring the Th2 (B19) gene into a host cell and associated transformation can be carried out by means of a commonly employed method; e.g., a calcium chloride method or an electroporation method for the case of the vectors which choose *E. coli* or *Bacillus subtilis* as their host cell; or a calcium phosphate method, an electroporation method, or a liposome injection method for the case of vectors which choose mammal or insect cells as their host cell.

The human Th2 (B19) protein of interest is accumulated by culturing the thus-obtained transformants according to a conventional method (the above-described transformants also fall within the scope of the present invention).

A medium used in the cultivation can be selected according to the properties of the host, as required. For example, if the host is *E. coli*, LB or TB mediums can be used as required. Further, if the host is a mammalian cell, an RPMI1640 medium can be used, as required.

The human Th2 (B19) protein can be isolated and purified from the culture products obtained by the cultivation according to a conventional method. For example, the human Th2 (B19) protein is isolated and purified from the culture products by various processing operations, utilizing physical and/or chemical properties of the human Th2 (B19) protein of the present invention.

More specifically, the isolation and purification of the protein can be accomplished through use of processing making use of a protein precipitant, ultrafiltration, gel filtration, high-performance liquid chromatography, centrifugal separation, electrophoresis, affinity chromatography using a specific antibody, or dialysis. These techniques may be used singly or in combination.

In this way, the human Th2 (B19) protein of the present invention can be isolated and purified.

In the Th2 (B19) gene expression system, the T cells or bone marrow cells isolated as a host from a patient can be utilized for so-called gene therapy by transforming the cells through use of the Th2 (B19) gene, and returning the resultant transformants to the patient.

In this case, virus vectors such as retroviruses or adenoviruses may be mentioned as the gene expression vectors.

The gene therapy which uses the foregoing transformants can be applied to patients whose diseases are principally due to a Th1/Th2 imbalance in which Th1 is dominant. More specifically, the transformants are administered to patients having, for example, multiple sclerosis or rheumatic arthritis. The Th1-dominant Th1/Th2 imbalance, which is the principal cause of these diseases, can be treated by gene therapy in which the administered transformants are caused to express human Th2 (B19) protein within the body of the patients.

E. Manufacture of an Antibody against the Human Th2 (B19) Protein of the Present Invention The present invention is also directed to an antibody against the human Th2 (B19) protein of the present invention.

The polyclonal antibody of the present invention can be manufactured from immune serum derived from animals which are immunized with the human Th2 (B19) protein serving as an immunogen.

The human Th2 (B19) protein used herein as the immunogen is not limited to any particular type of immunogen. As a matter of course, the human Th2 (B19) protein that is encoded by the Th2 (B19) gene [further including a Th2 (B19) gene having a nucleotide sequence partly altered] prepared in the above-described manner, can be used as the immunogen. Further, a fragment of the human (B19) protein which a partial fragment of the Th2 (B19) gene encodes, and a partial peptide of the human Th2 (B19) protein which is obtained through direct enzyme processing of the protein, or chemical synthesis of part of the human Th2 (B19) gene can be also used as an immunogen during manufacture of the polyclonal antibody of the present invention.

Cell lines derived from an animal which is of the same species and genealogy as the animal to be immunized are transformed with expression vectors which include genes encoding the human Th2 protein [including the human Th2 (B19) protein of the present invention] or the part thereof. Subsequently, the thus-transformed cells are transplanted to suitable animal to be immunized, whereby the polyclonal antibody of the present invention can be prepared. Specifically, the transformed cells continuously form the human Th2 protein within the body of the animal to which the transformed cells have been transplanted, and an antibody against the human Th2 protein is produced. This antibody may be also used as the polyclonal antibody of the present invention (Nemoto, T., et al., Eur. J. Immunol., 25, 3001 (1995)).

As is the case with the transplantation of the transformed cells, the polyclonal antibody can be manufactured by direct administration to the animal of an expression vector which expresses the human Th2 protein by intramascular or subcutaneous injection such that the human Th2 protein is continuously produced within the animal (Raz, E., et al., Proc. Natl. Acad. Sci. U.S.A., 91, 9519 (1994)).

The monoclonal antibody of the present invention can be manufactured in the same manner of manufacturing the polycolnal antibody of the present invention by the steps of producing hybridomas between myeloma cells and immunocytes of animals that are immunized, selecting clones which produce human-Th2-protein-recognizable antibodies, and culturing the thus-selected clones.

The animal to be immunized is not limited to any particular kind of animal. Mice and rats can be widely used. However, in the case of the manufacture of the monoclonal antibody, an animal is preferably selected in consideration of the compatibility of the animal with myeloma cells used for cell fusion.

Immunity can be induced by a commonly-employed method; e.g., by administering the immunogen to an animal to be immunized by intravenous injection, intradermal injection, subcutaneous injection, or intraperitoneal injection.

More specifically, the immunogen is administered to the animal several times every two to fourteen days by the above-described means, together with an ordinary adjuvant as desired. As a result, immune serum useful for manufacturing the polyclonal antibody or immunocytes useful for manufacturing the monoclonal antibody; e.g., immunized spleen cells, can be obtained.

In the case of manufacture of the monoclonal antibody, the following may be used as a myeloma cell which serves as a parent cell to be fused together with the immunocyte; e.g., SP2/0-Ag14, P3-NS1-1-Ag4-1, MPC11-45, 6. TG1. 7 (all of which are derived from mice); 210. RCY. Ag 1. 2. 3. (which is derived from rats); and SKO-007, and GM15006TG-A12 (both of which are derived from humans).

The immunized cells can be fused with the myeloma cells by known methods, for example, a method reported by Köhler and Milstein [Köhler, G. and Milstein, C., Nature, 256, 495 (1975)].

Specifically, the cell fusion is carried out within an ordinary culture medium to which promoting agents such as dimethylsulfoxide have been added as required in order to improve the efficiency of fusion, in the presence of a known ordinary fusion accelerator such as polyethylene glycol (PEG) or Sendai virus (HVJ) to thereby generate hybridomas.

A hybridoma of interest may be isolated by culturing it in an ordinary medium for selection purposes; e.g., a HAT (Hypoxanthine, Aminopterin, Thymidine) medium. In other words, a hybridoma of interest may be isolated by culturing fused cells in the medium for a sufficient period of time to kill cells other than the hybridoma. The thus-obtained hybridoma can be subjected to the screening of the objective monoclonal antibody and the cloning by an ordinary limiting dilution technique (This type of hybridoma also falls within the scope of the present invention.).

A monoclonal antibody-producing line of interest can be screened by a commonly-employed retrieving method; e.g., an ELISA method, a plaque method, a spot method, agglutination, an Ouchterlony test, or a RIA method.

The thus-prepared hybridoma which produces a human-Th2-protein-recognizable monoclonal antibody of interest can be subcultured in an ordinary medium or can be stored for a long period of time in liquid nitrogen.

A monoclonal antibody of interest is collected from the culture supernatant by culturing the hybridoma according to a customary method. Alternatively, the monoclonal antibody is collected by administering the hybridoma to an animal having compatibility with the hybridoma so as to induce the hybridoma to proliferate, and collecting ascites from the animal.

Further, monoclonal antibodies of interest may be obtained by culturing immunocytes in vitro in the presence of the human Th2 protein or portions of the protein, preparing through use of the cell fusion means hybridomas between the immunized cells and myeloma cells after lapse of a predetermined period, and screening the antibody-producing hybridomas (Reading, C. L., J. Immunol. Meth., 53, 261 (1982); Pardue, R. L., et al., J. Cell Biol., 96, 1149 (1983)).

Monoclonal antibodies of interest can alternatively be manufactured through direct use of the Th2 (B19) gene or portions of the gene without use of the human Th2 (B19) protein as an immunogen.

More specifically, it is also possible to manufacture monoclonal antibodies which specifically recognize the human Th2 (B19) protein, by directly immunizing an animal through use of the Th2 (B19) gene [at this time, a gene expression recombinant vector containing the Th2 (B19) gene can be used as an immunogen], and by using immunocytes of the gene-immunized animal.

The thus-obtained polyclonal or monoclonal antibodies may be purified by ordinary means such as salting out, gel filtration, or affinity chromatography.

The thus-obtained polyclonal or monoclonal antibodies exhibit specific reactivity against the human Th2 protein.

The polyclonal and monoclonal antibodies can be used as means for checking the Th1/Th2 balance within the body. In other words, the Th1/Th2 balance in the body is checked by determining the amount of human Th2 cells in a specimen through use of the antibodies in conjunction with ELISA, RIA, immunohistochemistry, flow cytometry, or the Western blotting technique. As mentioned in the section with the heading "Background Art", it becomes possible to more reliably ascertain variations in the symptoms of diseases to which a Th1/Th2 imbalance is of importance; e.g., atopic diseases or HIV diseases.

The thus-obtained polyclonal and monoclonal antibodies may also be used as antibodies for correcting, for example, a Th2-dominant Th1/Th2 imbalance.

With regard to antibodies derived from animals, they are acknowledged to have antigenicity against humans if directly administered to humans. Thus, the animal-derived antibodies are not suitable for administration to humans. For this reason, a variable region of the gene of the animal-derived monoclonal antibody is subjected to cloning, and a gene of this variable region and a gene of the constant region in a gene of a human antibody are fused together. A fused antibody can be manufactured by inducing expression of the thus-fused gene (Clarkson, T., et al., Nature, 352, 624 (1991)).

This technique may be applied to the foregoing monoclonal antibody; namely, the fused antibody formed by fusion of the variable region of the animal-derived monoclonal antibody with the constant region of the human antibody can be also used as an antibody for correcting, for example, the Th2-dominant Th1/Th2 imbalance.

EXAMPLES

The present invention will next be described by way of examples, which should not be construed as limiting the invention.

Example 1

Manufacture of a Th2 (B19) Gene of the Present Invention (1) Preparation of Helper T-cell Clones In order to chiefly induce human Th1 cells, 1 $\mu$g/ml of PHA (by EY laboratories), 50 ng/ml of rIFN-$\gamma$ (by Genzyme), and 5 ng/m of rIL-12 (by R&D Systems) were added to the culture of peripheral blood mononuclear cells (PBMC) ($10^6$ cells/ml) isolated from a healthy human. The mixture was cultured for five days. Independently, in order to chiefly induce human Th2 cells, 2% (v/v) mite extract (by Torii), 20 ng/ml of rIL-4 (by Genzyme), and 5 $\mu$g/ml of monoclonal anti-IFN-$\gamma$ antibody (by Genzyme) were added to the PBMC, and the resultant mixture was cultured for five days.

After lapse of five days, 40 U/ml of rIL-2 (by Shionogi) was added to each of the culture of PBMC. The PBMC were then further cultured for seven to ten days.

In order to isolate CD4$^+$ T cells from the cultured cells, the cultured cells were adsorbed by magnetic beads (by Dynal)

linked with anti-CD4 antibodies. The cells magnetically attracted to the magnetic beads were collected. The CD4+ T cells were dissociated from the magnetic beads by a magnetic bead separation reagent (by Dynal), whereby the CD4+ T cells were obtained.

Next, the thus-purified CD4+ T cells were cultured in 15% fetal calf serum-added RPMI 1640 medium supplemented with 0.5 µg/ml of PHA and 40 U/ml of rIL-2 in a 96-well microplate (0.5 cells/well). The medium was replaced with a fresh IL-2-added medium every three to four days. The surface marker of the cells which were observed to have proliferated was examined by immunofluorescence. Only the clones which were positive with respect to the CD4 were selected, and the thus-selected clones were taken as CD4+ T-cell clones of interest (Gianfranco, F. D. P., et al., J. Clin. Invest.,88, 346 (1991)).

Next, in order to examine the type of each of the CD4+ T-cell clones, the CD4+ T-cell clones (6×10⁵ cells/300 µl/well) were cultured for 24 hours on a 48-well plate coated with anti-CD3 antibodies (OKT3: by Ortho Pharmaceutical). Concentrations of IFN-γ and IL-4 in the culture supernatant were measured by ELISA which uses the respective monoclonal antibodies.

As a result, the clones that produced IL-4 but did not produce IFN-γ were taken as human Th2 clones. The results are shown in Table 1.

TABLE 1

| Clone | Donor | Primary Stimulation | Cytokine production (ng/ml) a) | | Th type |
|---|---|---|---|---|---|
| | | | IFN-γ | IL-4 | |
| 1P04 | KN | PHA | >50.0 | <0.2 | Th1 |
| 2P15 | KT | PHA | 19.2 | <0.2 | Th1 |
| 2P26 | KT | PHA | <0.5 | 9.0 | Th2 |
| KND4 | KN | Der b) | <0.5 | 4.9 | Th2 | a) The cells (6 × 10⁵ cells/300 µl/well) were cultured for 24 hours in a 48-well plate to which OKT3 had been immobilized. Concentrations of IFN-γ and IL-4 in the culture supernatant were measured by ELISA.
b) Mite extract (2) Preparation of a Subtracted cDNA Library Poly (A)+ RNA was respectively prepared from the human Th2 clones (2P26) and the human Th1 clones (2P15) obtained in (1), by a customary method making use of oligo dT latex (by Nippon Roche K.K.). While the poly (A)+ RNA was used as a template, about 300 ng of cDNA was generated for each poly (A)+ RNA through use of an oligo (dT) primer (by Pharmacia) and MMLV reverse transcriptase (by Pharmacia). Next, to cut each cDNA into a strand length suitable for an amplifying process of the PCR method, the cDNA was digested for five hours at 37° C. through use of restriction enzymes AluI (by Toyobo) (84U) and RSaI (by Toyobo) (48U), whereby each of the following PCR linkers which differ from one another was linked with each cDNA [Balzer, H. J., and Baumlein, H., Nucleic Acids Res., 22, 2853 (1994)]:

Linker for Human Th2:
5'-AGT TAC ACG TCT AGA ATG GCT-3' (Sequence ID No. 1)
3'-ATAG TCA ATG TGC AGA TCT TAC CGA -5' (Sequence ID No. 2)

Linker for Human Th1:
5'-CTC TTG CTT GAA TTC GGA CTA-3' (Sequence ID No. 3)
3'-ACAC GAG AAC GAA CTT AAG CCT GAT-5' (Sequence ID No. 4)

Only the cDNA fragments having the molecular-weight range from 0.2 Kbp to 2 Kbp were collected after fractionation by agarose gel electrophoresis. The thus-obtained 2P26-derived cDNA fragments and the 2P15-derived cDNA fragments were amplified by the PCR method through use of the following unique PCR primers (30 heat cycles each comprising: 94° C.×1 min.+50° C.×1 min.+72° C.×2 min.):

Primer for Human Th2:
5'-AGT TAC ACG TCT AGA ATG GCT-3' (Sequence ID No. 1)

Primer for Human Th1:
5'-CTC TTG CTT GAA TTC GGA CTA-3' (Sequence ID No. 3)

PCR products resulting from the PCR reaction were used as starting materials for subtraction purposes.

More specifically, an excessive amount of the PCR products (100 µg) derived from the biotin-labeled human Th1 (2P15) was added to the PCR products (5 µg) derived from the human Th2 (2P26). [Photoreactive biotin (100 µg) (by Vecter Laboratory) was added to DNA (100 µg). The mixture was placed stationary about 15 cm below a 160W Sun Lamp while being cooled on ice. The mixture was exposed to light for 15 mins. The non-reacted biotin was eliminated from the PCR product by butanol extraction. After repetition of these operations, biotinylated DNA was dissolved in Tris-EDTA buffer (TE), whereby biotin-labeling of the DNA was completed.] The resultant mixture was subjected to thermal denaturation at 100° C., so that each PCR product was dissociated into a single strand. The strands were hybridized with each other. Next, 100 µg of streptavidin (by Life Technologies) was added to the system, whereby cDNA derived from 2P15 which was hybridized with both free cDNA derived from 2P15 and that from 2P26 was adsorbed to the streptavidin, and the cDNA was eliminated from the system by extraction with phenol-chloroform. As a result of extraction, the cDNA containing a nucleotide sequence common to the cDNA derived from 2P15 was subtracted from the cDNA derived from 2P26, whereby subtraction for concentrating the 2P26-specific cDNA was completed.

The thus-concentrated 2P26-specific cDNA was repeatedly subjected to PCR amplification and subtraction in the above-described manner twice. After the cDNA specific for 2P26 had been concentrated further, it was subjected to PCR amplification in the same way as described above, whereby about 3 µg of cDNA was afforded.

The thus-prepared 2P26-specific cDNA was inserted to pBluescript SK(−) (by Stratagene) and cloned, thereby completing preparation of a subtracted cDNA library. Subsequently, a portion of the subtracted cDNA library was used to transform E. coli (E. coli JM 109 strain).

(3) Isolation of the Th2 (B19) Gene Fragments

The subtracted cDNA that was derived from 2P26 and obtained in step (2) and the subtracted cDNA that was derived from 2P15 and obtained in the same way were labeled with ³²P through use of a commercially available random priming labeling kit (by Takara), so that they were formed into radioactive probes.

Independently, the E. coli that had been transformed by part of the 2P26-derived cDNA library prepared in step (2) was seeded onto the plate. Two pairs of replica filters were formed with respect to colonies grown on the plate. These two pairs of replica filters were subjected to hybridization with the above-described two types of radioactive probes. They were washed with 0.1×SSC, and E. coli colonies containing cDNA homologous with the cDNA present in the probes were identified by autoradiography.

As a result of the screening of about 3,400 colonies according to this method, there were observed 201 colonies that did not provide a positive signal with respect to the subtracted 2P15-derived cDNA probe but provided a positive signal with respect to the subtracted 2P26-derived cDNA probe. With regard to these 201 cDNA clones, the difference between them was examined by a colony hybridization technique, whereby 60 independent clones which were not hybridized with one another were obtained.

For these 60 clones, the difference between 2P26 and 2P15 with regard to expression of mRNA was examined by the Northern blotting technique using the total RNA.

As a result, there were obtained 13 types of clones which did not express on 2P15 but expressed on 2P26.

Figure 1:
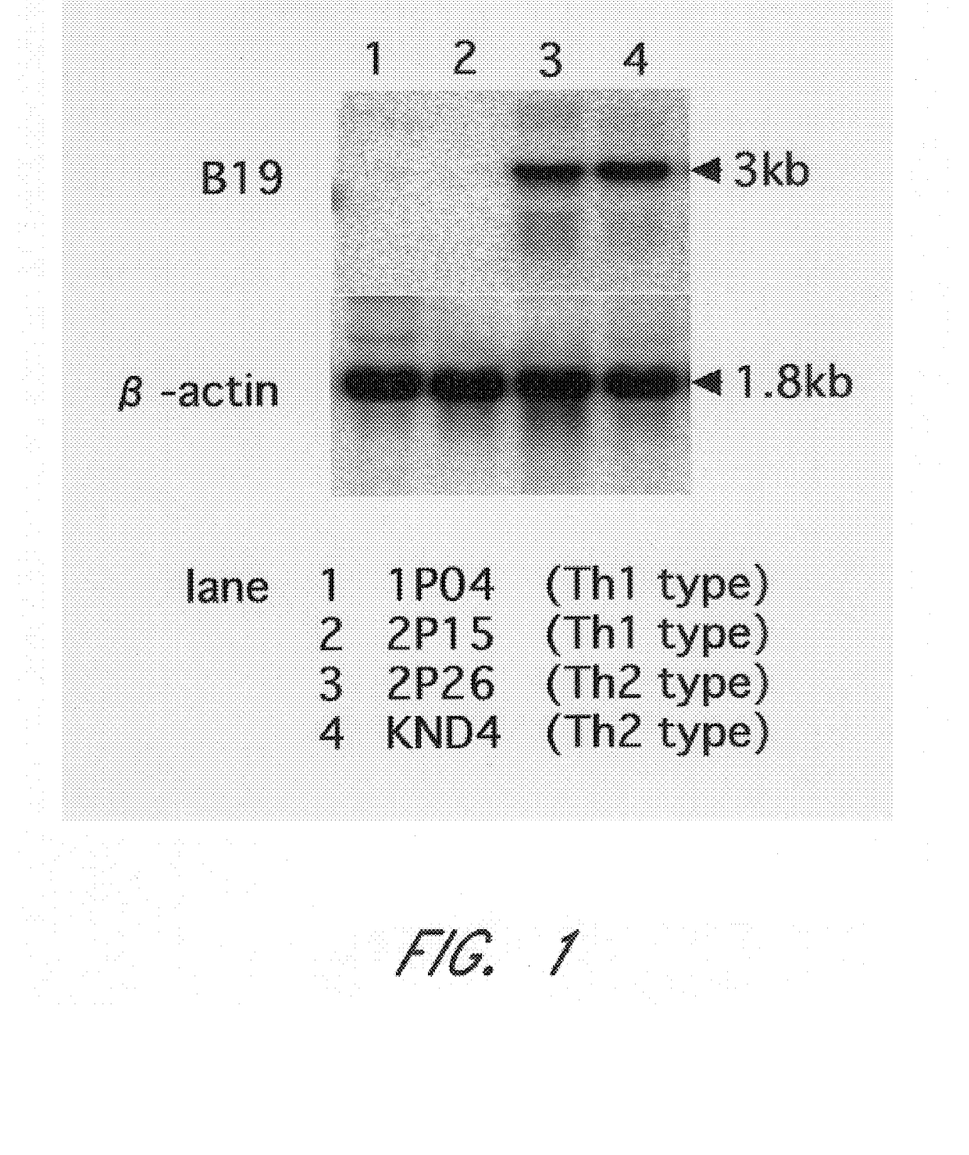
FIG. 1 is an autoradiogram showing the results of Northern blot of the clone B19.

To check the specificity of the cDNAs of the 13 types of clones against the human Th2, the difference in expression of mRNA between the plurality of human Th2 clone cells and human Th1 clone cells was examined by use of the Northern blotting technique. As a result, there were obtained several cDNA clones which were observed to have expression in common for only the human Th2 clone cells. FIG. 1 illustrates the results of Northern blotting of one (B19) of these clones.

In FIG. 1, it is evident that B19 mRNA has expressed in the aforementioned two human Th2 clones (2P26 and KND4; corresponding to lanes 3 and 4, respectively).

In contrast, B19 mRNA has not expressed in the human Th1 clone (1P04 and 2P15; corresponding to lanes 1 and 2, respectively).

The nucleotide sequence of cDNA clone B19 has been analyzed according to the dideoxy termination method making use of a fluorescent terminator (a kit manufactured by Perkin-Elmer was used).

It was revealed that the clone B19 had DNA of a novel nucleotide sequence.

A gene [Th2 (B19) gene of the present invention] containing a nucleotide sequence homologous with the above-described gene of clone B19 was cloned over its entire length.

(4) Cloning of the Th2 (B19) gene

In order to have the full length of the cDNA of interest cloned, a λ phage cDNA library was produced from cells which induce a high level of expression of B19 mRNA.

Briefly, the total RNA was extracted from the 2P26 cells, and poly(A)$^+$ RNA was purified by a routine method through use of oligo (dT) latex (Nippon Roche K.K.). Next, double-stranded cDNA was synthesized through use of a commercially available cDNA cloning kit (by Life Technologies), and the thus-synthesized cDNA was cloned at the EcoRI site of λ ZAPII (by Stratagene). Subsequently, the in vitro packaging of the λ phages was completed through use of a commercially available kit (by Stratagene). The packaged products were introduced into E. coli XL1-Blue MRF' (by Stratagene), whereby about 1×10$^5$ recombinant λ phages were obtained. The new cDNA fragments obtained in step (3) were labeled with $^{32}$P through use of a commercially available random primer labeling kit (by Takara). The labeled fragments, serving as radioactive probes, were used for the screening of the λ phage library by the plaque hybridization method.

As a result, 42 positive cDNA clones were obtained. Of these positive cDNA clones, three clones having the longest insert DNA were subjected to the nucleotide sequence analysis performed according to the dideoxy termination method that used a fluorescent terminator similar to that used in (3). As a result, it was confirmed that nucleotide sequences located in the overlapping areas between the three positive clones of cDNA completely matched up with one another, and that they had been derived from the same gene.

Of these three positive clones, the clone B19-1 having the longest cDNA was named B19 and used in the following procedures.

(5) Structure of the Th2 (B19) gene of the Present Invention cDNA incorporated into the clone B19 has a strand length of 2911 bp, which is close to the length of the mRNA (about 3 kbp) determined by the Northern blotting technique. The cDNA has at its 3'-terminal a poly(A)$^+$ additional signal and ten A's (adenine) which seem to be a part of the poly(A)$^+$.

It was expected that the longest open reading frame would start with ATG, the 113th from the 5'-terminal end, and terminate at the 1298th TGA and would encode a protein consisting of 395 amino acid residues. The nucleotide sequence (CCC ACG ATGT) in the vicinity of the initiation codon of the gene was similar to the consensus sequence CCA(G) CC ATGG of Kozak (Kozak, M., Nucleic Acids Res., 15, 8125 (1987)).

In view of the foregoing descriptions, the clone B19 was determined to contain substantially the full length of cDNA which starts from the 3'-terminal and reaches up to a part of the untranslated region on the 5'-terminal side via the full length of the coding region.

The gene having the cDNA of clone B19 is taken as the Th2 (B19) gene of the present invention, and the sequence of this gene is represented by sequence ID No. 5. Further, an amino acid sequence deduced to be encoded by this nucleotide sequence is represented by sequence ID No. 6.

The amino acid sequence is expressed by the single letter representation method as follows:

M S A N A T L K P L C P I L E Q M S R L Q S H S N - T S I R Y I D H A A V L L H G L A S L L G L - VENGVILFVVGCRMRQT VVTTWVLHLALSDLLA- SASLPFFTYFLAVGHSWELGTTFCKLHSSIFFLN MFASGFLLSAISLD RCLQVVRPVWAQNHRTVAAAH- K V C L V L W A L A V L N T V P Y F V F R D T I S R L D - GRIMCYYNVLLLNPG PDRDATCNSRQAALA- VSKFLLAFLVPLAIIASSHAAVSLRLQHRGRRRPGRF VRLVAAVVAAFA LCWGPYHVFSLLEARAHANPGLR- P L V W R G L P F V T S L A F F N S V A N P V L Y V - LTCPDMLRKLRRSLR TVLESVLVDDSELGGAGSSR- RRRTSSTARSASPLALCSRPEEPRGPARLLGWLLGS CAASPQTGPLNRALSSTSS

[In the above-described amino acid sequence, A: alanine, V: valine, L: leucine, I: isoleucine, P: proline, F: phenylalanine, W: tryptophan, M: methionine, G: glycine, S: serine, T: threonine, C: cysteine, Q: glutamine, N: asparagine, Y: tyrosine, K: lysine, R: arginine, H: histidine, D: asparatic acid, and E: glutamic acid]

The transformant consisting of E. coli (E. coli K12-JM109 strain) having the gene of the present invention integrated therein is deposited with the National Institute of Bioscience and Human Technology, Agency of Industrial Science and Technology, Japan Ministry of International Trade and Industry (1-3, Tsukuba-shi 1-chome, Ibaraki-ken, Japan 305) under accetion No. FERM P-15616 (accepted on May 15, 1996).

(6) In vitro Transcription and Translation of Th2 (B19) gene of the Present Invention While the Th2 (B19) gene of the present invention was used as a template, RNA was synthesized with T7 RNA polymerase through use of a commercially available kit (by Stratagene). Subsequently, the RNA was translated in vitro in the presence of $^{35}$S-methionine through use of commercially available rabbit reticulocyte extract (by Promega Biotech).

Figure 2:
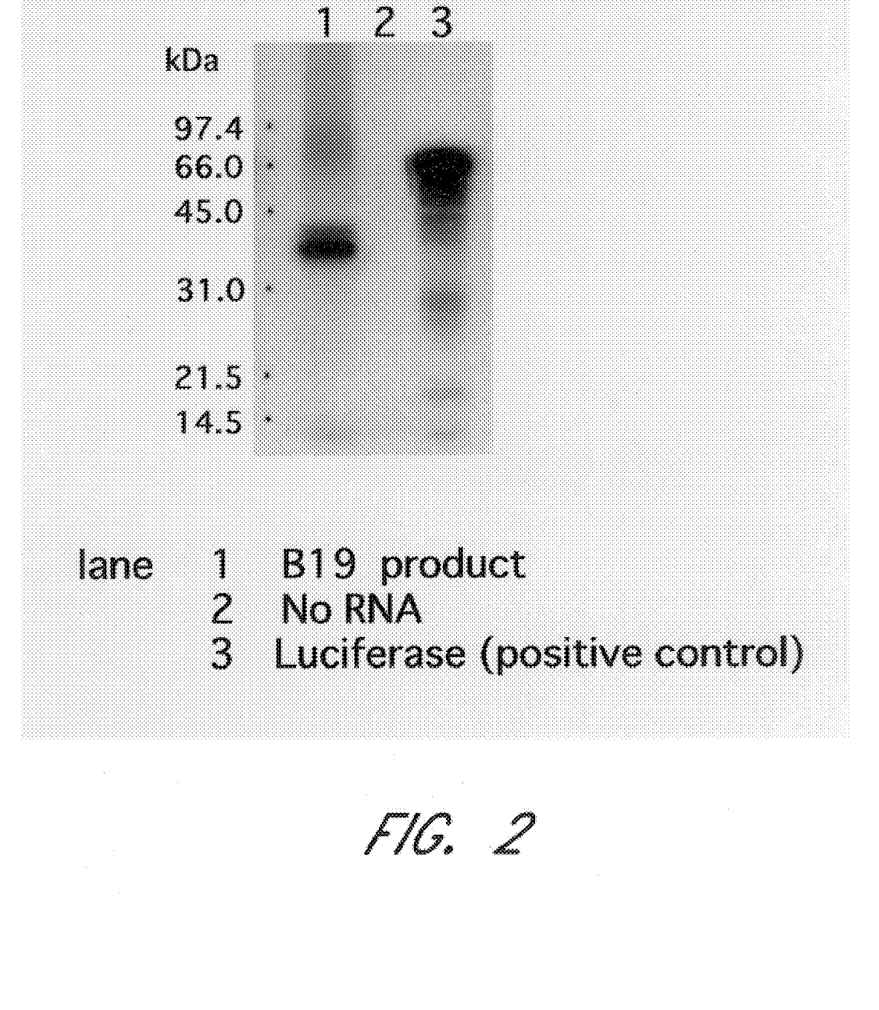
FIG. 2 is an autoradiogram showing an in vitro translation product of the Th2 (B19) gene of the present invention.

According to the Laemmli method, the thus-translated product was analyzed by SDS polyacrylamide gel electrophoresis. As a result, it was confirmed that there had been formed a protein having a molecular weight which is similar to the predicted molecular weight of 43 kd (see FIG. 2).

(7) Tissue Specificity of Expression of mRNA

To examine the tissue specificity of expression of the mRNA derived from the Th2 (B19) gene of the present invention, the total RNA of cell lines derived from various tissues was subjected to Northern blot analysis.

Figure 3:
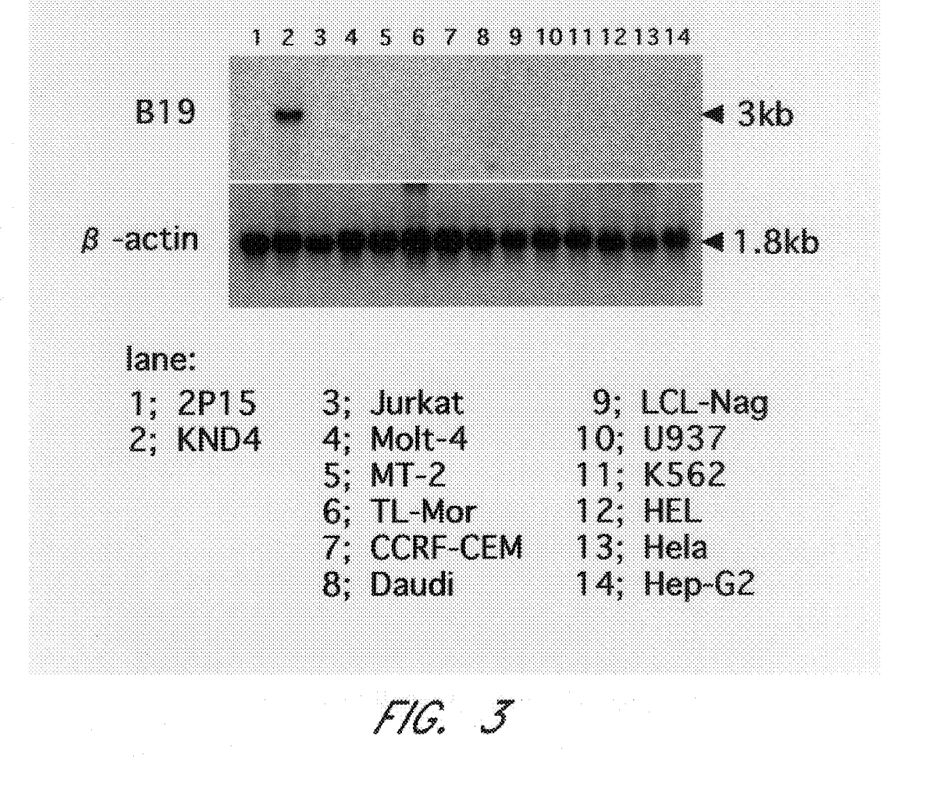
FIG. 3 is an autoradiogram showing the results of Northern blot which indicates the tissue specificity of expression of mRNA derived from the Th2 (B19) gene of the present invention.

As a result, expression of the mRNA derived from the Th2 (B19) gene could not be confirmed in any of the cell lines (FIG. 3).

Thus, it has become evident that expression of the Th2 (B19) gene is limited to a specific cell that includes the Th2 cells.

Example 2

Manufacture of Antibodies Against the Human Th2 (B19) Protein of the Present Invention (1) Manufacture of Th2 (B19) Gene Expression Vector It is difficult to predict the expression level of the introduced gene in the mammalian cell because the expression level tends to be widely different dependent on the combination of a host cell and an expression vector to be used. Therefore, the Th2 (B19) gene was incorporated into some expression vectors for which high expression was expected.

More specifically, an insert DNA containing the coding region of the Th2 (B19) gene was excised from plasmid DNA (pBluescript SK(–), cDNA clone B19) containing the full length of the Th2 (B19) gene (represented by sequence ID No. 5) through use of restriction enzymes which are suitable for the cloning sites of the objective expression plasmides. The insert DNA was then purified by agarose gel electrophoresis.

Th2 (B19) gene of the present invention obtained in such a way was inserted at each of the cloning sites of pRc/CMV, pcDL-SRα, pREP9, etc., so that various kinds of expression vectors (plasmids) of the Th2 (B19) gene of the present invention for a mammalian cell of interest were obtained.

(2) Manufacture of Transformed Cell Expressing Th2 (B19) Gene of the Present Invention 50 µg of each of the human Th2 (B19) protein expression plasmids of the present invention obtained in (1) was introduced into $10^7$ cells of each of Jurkat cells, 293 cells (these being from a human T cell line and a human renal cell line), BW 5147 (from a mouse T cell line), and TART-1 (from a rat T cell line).

The cells were seeded onto a 96-well plate at 500 to 1000 cells per well, and cultured in a medium containing Geneticin (by Sigma) for 2 to 3 weeks to select transformed cells. The expression level of the Th2 (B19) gene of the present invention was confirmed by Northern blot technique.

The transformed cells having highest expression level of the Th2 (B19) gene of the present invention were selected from a large number of the transformed cells with respect to each cell line, and then cloning operation was carried out in which the cells were seeded onto a 96-well plate at 0.3 cell per well.

As a result, Jurkat/B19, 293/B19, BW/B19 and TART/B19 cell lines which were expressing the Th2 (B19) gene of the present invention stably and at a high level were obtained.

Amoung the thus-obtained transformed cells of the Th2 (B19) gene of the present invention, $10^7$ cells of the TART/B19 cells were injected into a peritoneal cavity once every week a total of five times to immunize 8-week-old Wister rats (female) (Nemoto, T., Eur. J. Immunol., 25, 3001 (1995)).

(3) Preparation of Hybridomas

After three days have passed since the rat was finally immunized, $3 \times 10^8$ spleen cells of the rat were mixed with $5 \times 10^7$ cells of mouse myeloma cell line SP 2/0-Ag14. They were fused together through use of a 50% polyethylene glycol (a mean molecular weight of 1500) PBS solution (by Sigma). The fused cells were seeded onto a 96-well plate at $1 \times 10^5$ cells/well, and, a HAT reagent (by Sigma) was added from the next day and the selective culture were carried out for ten days. As a result, the proliferation of hybridomas was observed in substantially all wells.

The presence/absence of monoclonal antibodies specific to the human Th2 (B19) protein of the present invention in a culture supernatant of each hybridoma was confirmed by a membran fluorescent antibody technique using TART-1 cells and TART/B19 cells.

More specificaly, 50 µl of the culture supernatant of each hybridoma was added to $5 \times 10^5$ cells of each of TART-1 cells and TART/B19 cells and thoroughly mixed to react each other for 20 min at room temperature. After washing twice with PBS containing 0.5% BSA, the cells were reacted with phycoerythrin-labeled goat anti-rat immunoglobulin antibody (by Bio Source International) for 20 min at room temperature. After the reaction, the cells were washed again twice with PBS containing 0.5% BSA and then floated in a small amount of 50% glycerin/PBS and sealed between a slide glass and a cover glass. The fluorescent strength on the cell membranes was observed under a fluorescence microscope (by Olympus).

As a result, the supernetants which had the reactivity to only the TART/B19 cell membrane but not to the TART-1 cell membrane were taken as positive samples.

(4) Manufacture of Monoclonal Antibodies

With regard to the culture supernatants of the hybridoma which were admitted to be positive as a result of the above screening, the specificity of the supernatants to the human Th2 (B19) protein of the present invention was comfirmed with the above plural number of cell panels.

More specificity, with regard to Jurkat and Jurkat/B109, 293 and 293/B19, and BW5147 and BW/B19, the specificity of reaction was confirmed by a membrane fluorescent antibody technique as described above.

With regard to the hybridomas which were confirmed to have the specificity in all cell panels as described above, the cloning operation in which the cells were seeded onto a 96-well plate at 0.3 cell per well was repeated two or three times, so that the hybridomas which produced monoclonal antibodies were produced.

One of these hybridomas (Rat Hybridoma BM16) was deposited with the National Institute of Bioscience and Human Technology, Agency of Industrial Science and Technology, Japan Ministry of International Trade and Industry (1-3, Tsukuba-shi 1-chome, Ibaraki-ken, Japan 305) under accetion No. FERM P-16216 (accepted on May 8, 1997).

Using this monoclonal antibody, Th2 clone cells were stained by a membrane fluorescent antibody technique as described above. The results of analysis by a flow cytometer are shown in FIG. 4.

Figure 4:
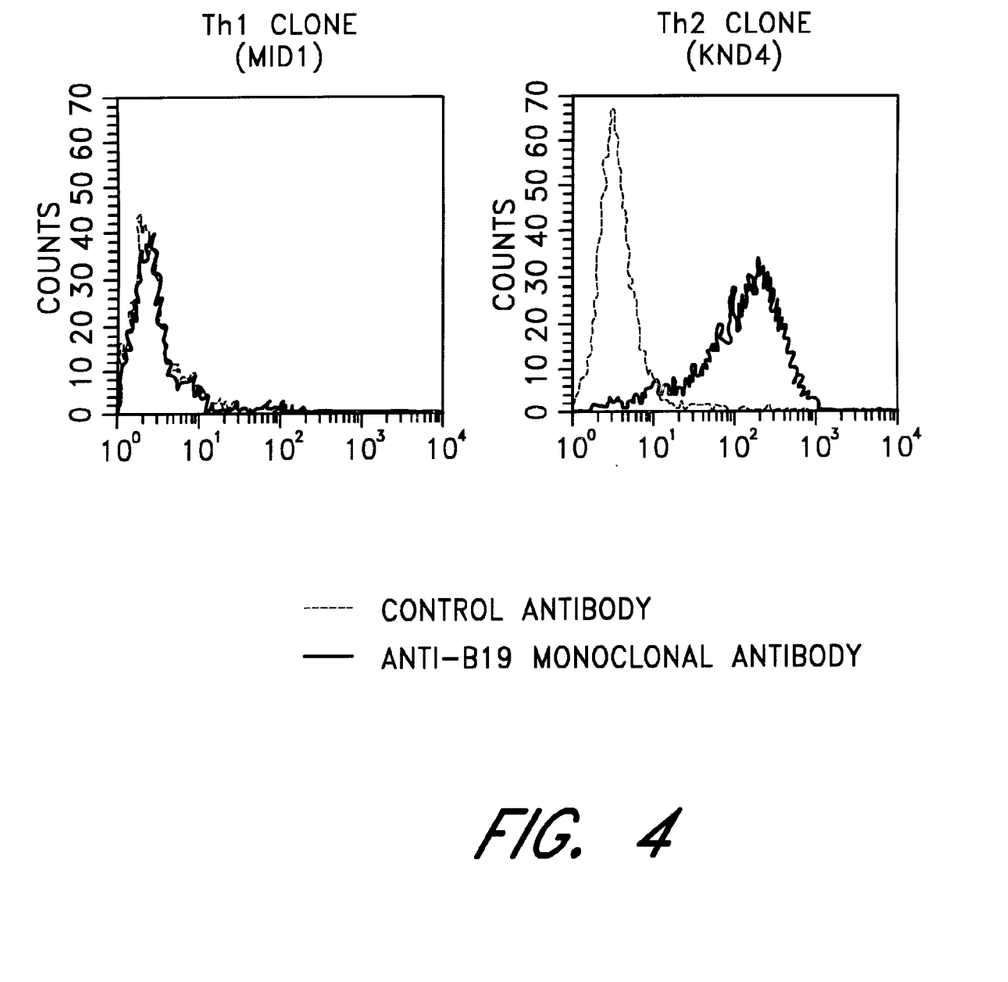
FIG. 4 shows the analyses with a flow cytometer after staining the Th1 clone and Th2 clone cells by a membrane fluorescent antibody technique with the monoclonal antibody of the present invention.

In FIG. 4, it was confirmed that the product of the Th2 (B19) gene of the present invention is expressed on the cell membrane and the product is more dominantly expressed in the Th2 cells than in the Th1 cells.

Industrial Applicability:

By virtue of the present invention, there are provided a human-Th2-specific gene and a human-Th2-specific protein which are important factors of means for specifying the condition and type of immune-related diseases on the basis of the knowledge about the polarization of distribution of Th1/Th2 subsets.

Further, there are provided a recombinant vector for expressing a gene which contains the human-Th2-specific gene and a transformant which is transformed by the above-described recombinant vector.

Moreover, there are provided monoclonal and polyclonal antibodies which use the human-Th2-specific protein as an antigen, and a hybridoma which produces the monoclonal antibody.

What is claimed is:

1. A human-Th2-specific protein comprising an amino acid sequence set forth in sequence ID No. 6.

* * * * *